US009126218B2

(12) United States Patent
Sasaki et al.

(10) Patent No.: US 9,126,218 B2
(45) Date of Patent: Sep. 8, 2015

(54) ULTRASONIC ATOMIZING UNIT

(75) Inventors: Takeshi Sasaki, Takarazuka (JP); Daisuke Takahata, Ageo (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 1 day.

(21) Appl. No.: 13/883,840

(22) PCT Filed: Nov. 7, 2011

(86) PCT No.: PCT/JP2011/076124
§ 371 (c)(1), (2), (4) Date: Dec. 27, 2013

(87) PCT Pub. No.: WO2012/063951
PCT Pub. Date: May 18, 2012

(65) Prior Publication Data

US 2014/0151461 A1 Jun. 5, 2014

(30) Foreign Application Priority Data

Nov. 9, 2010 (JP) ................................ 2010-251328

(51) Int. Cl.
*B05B 17/06* (2006.01)
*A61M 11/00* (2006.01)
(Continued)

(52) U.S. Cl.
CPC ............. *B05B 17/06* (2013.01); *B05B 17/0646* (2013.01); *B05B 17/0684* (2013.01)

(58) Field of Classification Search
CPC B05B 17/06; B05B 17/0607; B05B 17/0615; B05B 17/0638; B05B 17/0646; B05B 17/0684; A61M 11/005; A61M 15/0085
USPC ....................... 239/4, 102.1, 102.2, 145, 326; 128/200.14, 200.16, 200.18; 347/68, 347/70
See application file for complete search history.

(56) References Cited

U.S. PATENT DOCUMENTS 6,769,626 B1 8/2004 Haveri
8,296,993 B2 10/2012 Modlin et al.
(Continued)

FOREIGN PATENT DOCUMENTS

EP 1 332 006 B1 8/2003
EP 1 382 399 A1 1/2004
EP 2 100 670 A1 9/2009
JP S59-032971 A 2/1984
JP 2006-281170 10/2006
(Continued)

OTHER PUBLICATIONS

Written Opinion of the International Searching Authority PCT/JP2011/076124 dated Apr. 2, 2012.
(Continued)

*Primary Examiner* — Darren W Gorman
(74) *Attorney, Agent, or Firm* — Foley & Lardner LLP

(57) ABSTRACT

An ultrasonic atomizing unit is provided which can spray fine particles of a liquid farther without greatly increasing a voltage applied to a piezoelectric vibrator and using a fan. An annular atomizing member (1) is provided and ultrasonically vibrates a vibrating plate (12) with a piezoelectric vibrator (11) to atomize a liquid. The atomizing member (1) is elastically sandwiched and held by a casing (3) through a pair of annular elastic rings (2) that are in contact with the atomizing member (1). A maximum facing width in a radial direction between each annular elastic member and one surface of the atomizing member (1) on one side in the radial direction from the center of the atomizing member (1) is 40% of a radial direction width of the piezoelectric vibrator (11) on one side in the radial direction from the center of the piezoelectric vibrator (11).

13 Claims, 7 Drawing Sheets

(51) Int. Cl.
*A61M 15/00* (2006.01)
*B05B 17/00* (2006.01)

(56) References Cited

U.S. PATENT DOCUMENTS

| | | | | |
|---|---|---|---|---|
| 2006/0207591 | A1 | 9/2006 | Gallem et al. | |
| 2007/0237498 | A1 | 10/2007 | Helf et al. | |
| 2008/0006264 | A1 * | 1/2008 | Gallem et al. | 128/200.14 |
| 2008/0011875 | A1 | 1/2008 | Sipinski et al. | |
| 2008/0073447 | A1 * | 3/2008 | Wang et al. | 239/302 |
| 2008/0308096 | A1 * | 12/2008 | Borgschulte et al. | 128/200.14 |
| 2009/0224064 | A1 | 9/2009 | Brodbeck et al. | |
| 2010/0319685 | A1 | 12/2010 | Yu | |
| 2012/0111970 | A1 * | 5/2012 | Hogan et al. | 239/102.2 |

FOREIGN PATENT DOCUMENTS

| | | | |
|---|---|---|---|
| WO | WO 03/097126 | A2 | 11/2003 |
| WO | WO 2006/127181 | A2 | 11/2006 |
| WO | WO 2010/134164 | A1 | 11/2010 |
| WO | WO 2011/061479 | A1 | 5/2011 |
| WO | WO 2011/083379 | A1 | 7/2011 |

OTHER PUBLICATIONS

International Search Report PCT/JP2011/076124 dated Apr. 2, 2012.

European Office Action dated Apr. 7, 2015 issue in Application No. 11 805 245.5.

U.S. Office Action dated May 7, 2015 issued in U.S. Appl. No. 14/366,430.

* cited by examiner

--PRIOR ART--

--PRIOR ART--

--PRIOR ART--

ULTRASONIC ATOMIZING UNIT

TECHNICAL FIELD

The invention relates to an ultrasonic atomizing unit for atomizing a liquid such as water or a chemical liquid by means of ultrasonic vibrations.

BACKGROUND ART

Conventionally, as an ultrasonic atomizing unit for use in an ultrasonic atomizing device, a unit is known which has a structure in which an atomizing member including a piezoelectric vibrator and a vibrating plate mounted to the piezoelectric vibrator is elastically sandwiched and held by a casing through elastic members formed from an elastic material (e.g., see Patent Literature 1).

FIG. 5 is a cross-sectional view illustrating an example of the ultrasonic atomizing unit described in Patent Literature 1, and FIG. 6 is an exploded perspective view of the ultrasonic atomizing unit. The ultrasonic atomizing unit includes: an atomizing member 100 including a piezoelectric vibrator 101 having an opening 101*a* at a central part thereof and a vibrating plate 102 mounted to the piezoelectric vibrator 101; a pair of elastic members 103 that are arranged so as to extend along both surfaces, respectively, of the atomizing member 100; and a casing 104 as a holding member that accommodates the atomizing member 100 and the elastic members 103 therein.

The piezoelectric vibrator 101 is formed from a circular thin plate-shaped piezoelectric ceramic. When a high-frequency voltage is applied to electrodes 101*b* provided on the upper and lower surfaces of the piezoelectric vibrator 101, ultrasonic vibrations occur such that the piezoelectric vibrator 101 expands and contracts in a radial direction thereof. In addition, the vibrating plate 102 is formed from a circular thin plate-shaped metal, and is mounted to the lower surface of the piezoelectric vibrator 101 so as to cover the opening 101*a* of the piezoelectric vibrator 101. The vibrating plate 102 has a large number of micropores 102*a* formed in a portion thereof which faces the opening 101*a*.

The pair of elastic members 103 are formed from annular flat plate-shaped rubbers, and are adhered to both surfaces, respectively, of the atomizing member 100 so as to be in surface contact therewith. In addition, the casing 104 has a hollow circular plate shape with an opening at a central part thereof, and elastically sandwiches and holds therein the atomizing member 100 through the pair of elastic members 103. The casing 104 is divided into two upper and lower portions that are separable from each other.

According to the above conventional ultrasonic atomizing unit, a high-frequency voltage is applied to the piezoelectric vibrator 101 to ultrasonically vibrate the piezoelectric vibrator 101 to ultrasonically vibrate the vibrating plate 102, whereby a liquid supplied to the micropore 102*a* portion of the vibrating plate 102 can be atomized and sprayed.

Patent Literature 1 also discloses an ultrasonic atomizing unit in which instead of the thin plate-shaped elastic members 103, a pair of first elastic members 105 having rubber band shapes and a pair of second elastic members 106 having outer diameters larger than those of the first elastic members 105 are used, and the elastic members 105 and the elastic members 106 are arranged so as to extend along outer peripheral edges and opening edges of both surfaces, respectively, of the atomizing member 100 (see FIG. 7).

CITATION LIST

Patent Literature

[PTL 1] Japanese Laid-Open Patent Publication No. 2006-281170 (FIGS. 12 to 14)

SUMMARY OF THE INVENTION

Technical Problem

Depending on a type of an atomized liquid and usage environment, the conventional ultrasonic atomizing unit may be required to spray fine particles of a liquid farther. In this case, a voltage applied to the piezoelectric vibrator 101 is greatly increased or a blast fan is used, thereby spraying fine particles of a liquid farther.

However, when a voltage applied to the piezoelectric vibrator 101 is greatly increased, there is a problem that a drive circuit for generating a high-frequency voltage is made large in size, the amplitude of vibrations of the vibrating plate 102 is increased, and thus the life of the vibrating plate 102 is reduced. In addition, when a blast fan is used, there is a problem that fine particles of a liquid excessively spread and the device is made large in size.

The invention is made in view of the above problems, and an object of the invention is to provide an ultrasonic atomizing unit that can spray fine particles of a liquid farther without greatly increasing a voltage applied to a piezoelectric vibrator and using a fan.

Solution to the Problems

An ultrasonic atomizing unit according to the invention includes: an atomizing member including a circular thin plate-shaped piezoelectric vibrator having an opening at a central part thereof, and a vibrating plate that has a large number of micropores extending therethrough in a thickness direction thereof and is arranged so as to face the opening and so as to extend along one surface of the piezoelectric vibrator, the atomizing member ultrasonically vibrating the vibrating plate with the piezoelectric vibrator to atomize a liquid; a pair of annular elastic members arranged so as to extend along both surfaces, respectively, of the atomizing member and so as to be concentric with the atomizing member; and a holding member elastically sandwiching and holding the atomizing member through the pair of elastic members. A maximum facing width in a radial direction between each annular elastic member and one surface of the atomizing member on one side in the radial direction from a center of the atomizing member is 40% of a radial direction width of the piezoelectric vibrator on one side in the radial direction from a center of the piezoelectric vibrator.

According to the ultrasonic atomizing unit having such a configuration, since the maximum facing width in the radial direction between each annular elastic member and the one surface of the atomizing member is 40% of the radial direction width of the piezoelectric vibrator, suppression of vibrations of the atomizing member can be prevented. Thus, fine particles of the liquid atomized by the atomizing member can be sprayed far.

In other words, the inventor of the present application conducted thorough research for the reason why a conventional ultrasonic atomizing unit cannot spray far fine particles of an atomized liquid. As a result, the inventor found that the reason is that since, in the conventional ultrasonic atomizing unit, annular flat plate-shaped elastic members having a large width dimension in a radial direction thereof are arranged so as to extend over the entireties of both surfaces of an atomizing member, or two pairs of rubber band-shaped elastic members are arranged so as to extend along opening edges and outer peripheral edges of both surfaces of a piezoelectric vibrator, vibrations of the piezoelectric vibrator (atomizing member) are partially suppressed by the elastic members. The inventor completed the invention of the present application on the basis of this finding.

In the ultrasonic atomizing unit, the vibrating plate may have, at a central part thereof, a convex portion projecting to a spray side or a convex portion projecting opposite to a spray side.

Preferably, where a diameter of a base end part of the convex portion is indicated by R1 and a diameter of the opening at the central part of the piezoelectric vibrator is indicated by R2, a relation between R1 and R2 is:

$$R1 \leq (4/5) \cdot R2.$$

This is because when the relation between R1 and R2 is R1>(4/5)·R2, the radial direction dimension of a planar part of the portion, of the vibrating plate, which faces the opening at the central part of the piezoelectric vibrator is excessively small, and thus it is difficult for the planar part to deform in a bending manner with ultrasonic vibrations of the piezoelectric vibrator and fine particles of an atomized liquid cannot more effectively be sprayed farther.

In the ultrasonic atomizing unit, preferably, the vibrating plate is not flat plate type but has, at a central part thereof, a convex portion projecting to a spray side.

In this case, fine particles of the liquid atomized by the atomizing member can more effectively be sprayed far than in the case of a vibrating plate that does not have the convex portion.

In the ultrasonic atomizing unit, preferably, the annular elastic members are O-rings.

In this case, since the O-rings are in line contact with the atomizing member, suppression of vibrations of the atomizing member can more effectively be prevented. Thus, fine particles of the liquid atomized by the atomizing member can be sprayed farther.

Preferably, cross-sectional diameters of the O-rings are in the range of 0.5 to 2.0 mm.

In this case, fine particles of the liquid atomized by the atomizing member can be sprayed farther.

In the ultrasonic atomizing unit, preferably, a minimum facing width in the radial direction between each annular elastic member and one surface of the atomizing member on one side in the radial direction from the center of the atomizing member is 5% of the radial direction width of the piezoelectric vibrator on one side in the radial direction from the center of the piezoelectric vibrator.

In this case, since the facing width ratio is equal to or greater than 5%, the atomizing member can stably be supported by the elastic members. Thus, the liquid can stably be atomized.

Further, in the ultrasonic atomizing unit, preferably, the piezoelectric vibrator has a thickness of 0.1 to 4.0 mm and an outer diameter of 6 to 60 mm, the vibrating plate has a thickness of 0.02 to 2.0 mm and an outer diameter of 6 to 60 mm, and the micropores have pore sizes of 3 to 150 μm.

According to the ultrasonic atomizing unit, fine particles of the liquid atomized by the atomizing member having a relatively small size can be sprayed farther.

Preferably, each annular elastic member has a hardness of 20 to 90 IRHD. In this case, the atomizing member can effectively be held, and thus the liquid can more stably be atomized.

It should be noted that values of IRHD in the present application are values according to the international rubber hardness M method.

Advantageous Effects of the Invention

The ultrasonic atomizing unit according to the invention can spray fine particles of the liquid farther without greatly increasing a voltage applied to the piezoelectric vibrator and using a fan.

DESCRIPTION OF EMBODIMENTS

Hereinafter, embodiments of an ultrasonic atomizing unit according to the invention will be described with reference to the accompanying drawings.

Figure 1:
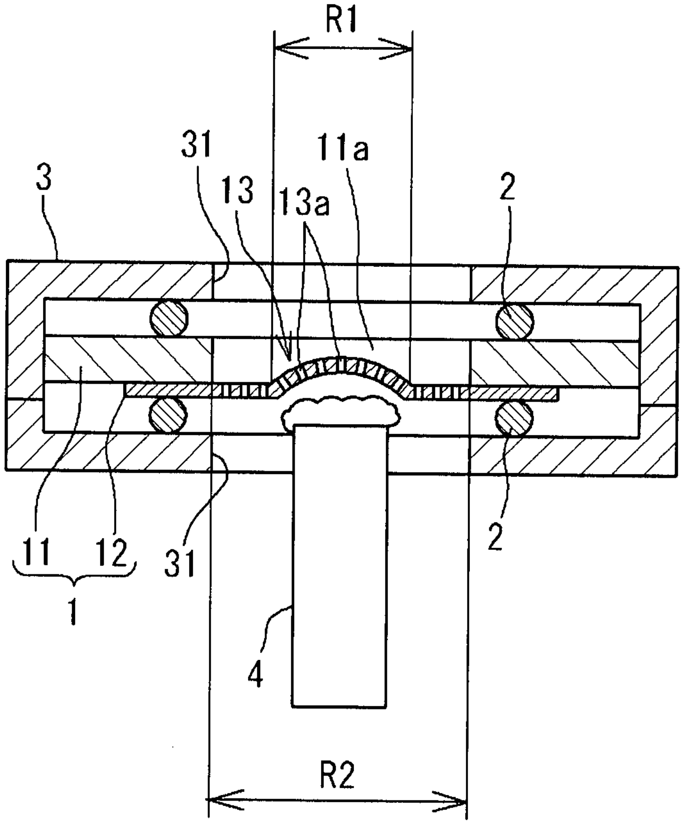
FIG. 1 is a cross-sectional view illustrating an embodiment of an ultrasonic atomizing unit according to the invention.
Figure 2:
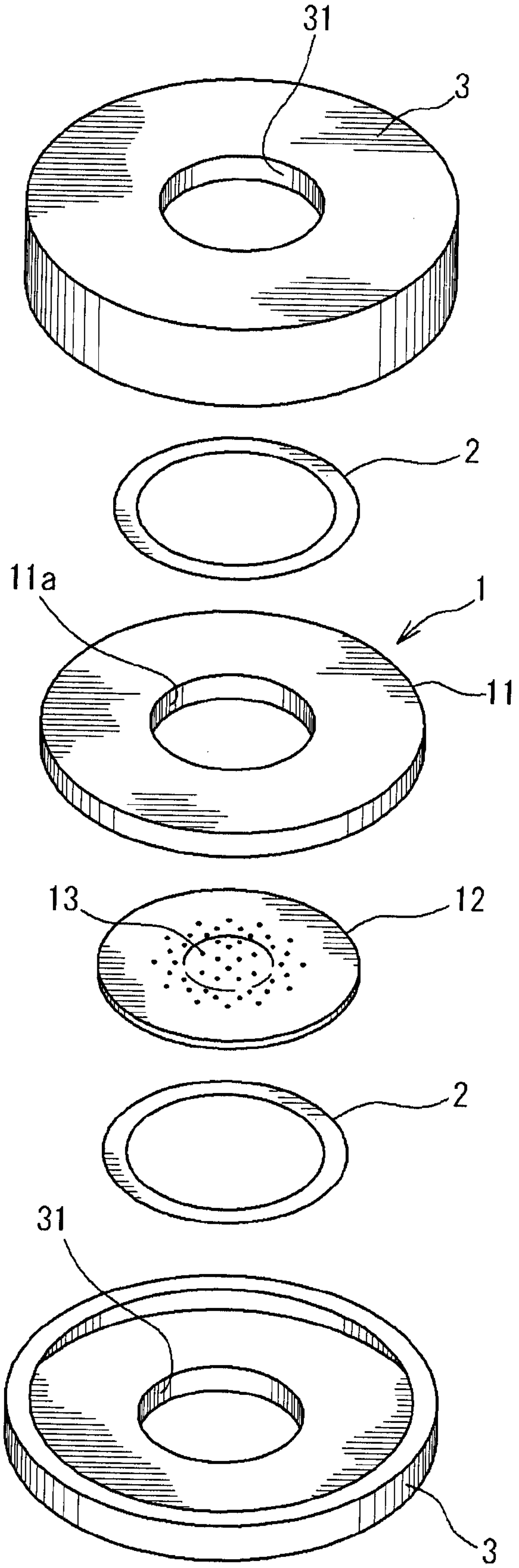
FIG. 2 is an exploded perspective view of the ultrasonic atomizing unit.

FIG. 1 is a cross-sectional view illustrating an embodiment of the ultrasonic atomizing unit according to the invention. The ultrasonic atomizing unit includes: an atomizing member 1 that ultrasonically vibrates a vibrating plate 12 with a piezoelectric vibrator 11 to atomize a liquid such as water or a chemical liquid; a pair of elastic rings 2 as annular elastic members that are arranged so as to extend along both surfaces, respectively, of the atomizing member 1; and a casing 3 as a holding member that elastically sandwiches and holds the atomizing member 1 through the pair of elastic rings 2. A liquid absorbing core 4 for supplying a liquid such as a chemical agent to the vibrating plate 12 is provided so as to be in contact with or adjacent to the vibrating plate 12.

The piezoelectric vibrator 11 of the atomizing member 1 is composed of a circular thin plate-shaped piezoelectric ceramic having an opening 11*a* formed at a central part thereof. The piezoelectric vibrator 11 is polarized in a thickness direction thereof. When a high-frequency voltage is applied to electrodes that are formed on both surfaces of the piezoelectric vibrator 11 and not shown, micro vibrations occur in a radial direction. As the piezoelectric vibrator 11, for example, one is selected which has a small size with a thickness of 0.1 to 4.0 mm and an outer diameter of 6 to 60 mm and for which the frequency (drive frequency) of a high-frequency voltage is 30 to 500 KHz.

The vibrating plate 12 is formed from, for example, nickel and has a circular thin plate shape. In FIG. 1, the vibrating plate 12 is joined (fixed) to the lower surface of the piezoelectric vibrator 11 so as to cover the opening 11*a* of the piezoelectric vibrator 11 and so as to be concentric with the piezoelectric vibrator 11. As the vibrating plate 12, for example, one is selected as appropriate which has a thickness of 0.02 to 2.0 mm and an outer diameter of 6 to 60 mm, whose outer diameter is larger than the inner diameter dimension of the opening 11*a* of the piezoelectric vibrator 11, and whose size corresponds to the size of the piezoelectric vibrator 11.

The vibrating plate 12 has a large number of micropores 13*a* formed in a portion thereof which faces the opening 11*a* and extending therethrough in a thickness direction thereof. The pore sizes of the micropores 13*a* are 3 to 150 μm. In addition, the vibrating plate 12 has, at a central part thereof, a convex portion 13 formed with a curved surface from its top toward its bottom. The convex portion 13 is a dome-shaped portion projecting upwardly (in a direction in which a liquid is sprayed). With expansion and contraction (vibrations) of the piezoelectric vibrator 11 in the radial direction, a part of the convex portion 13 ultrasonically vibrates in the vertical direction. Where the diameter of a base end part that is a rising part of the convex portion 13 is indicated by R1 and the diameter (inner diameter) of the opening 11*a* at the central part of the piezoelectric vibrator 11 is indicated by R2, the relation between R1 and R2 is:

$$R1 \leq (4/5) \cdot R2.$$

Due to this, a planar portion around the convex portion 13 can easily be deformed in a bending manner with ultrasonic vibrations of the piezoelectric vibrator 11. Thus, fine particles of an atomized liquid can be sprayed farther.

Only one pair of the elastic rings 2 are provided. The pair of elastic rings 2 are in contact with the upper and lower surfaces of the atomizing member 1 so as to be elastically deformed between the casing 3 and the upper surface of the atomizing member 1 and between the casing 3 and the lower surface of the atomizing member 1, respectively, and so as to be concentric with the atomizing member 1. As each elastic ring 2, an O-ring having a cross-sectional diameter of 0.5 to 3 mm and more preferably a cross-sectional diameter of 0.5 to 2.0 mm is suitably used. When O-rings having such cross-sectional diameters are used, the elastic rings 2 can be in thin line contact with the atomizing member 1. Thus, fine particles of an atomized liquid can more effectively be sprayed far.

The hardness of each elastic ring 2 is 20 to 90 IRHD, more preferably 30 to 90 IRHD. Due to this, the atomizing member 1 can be held with an appropriate elastic force, and excessive vibrations of the atomizing member 1 can effectively be suppressed. Thus, a liquid can more stably be atomized.

The elastic ring 2 that is in contact with the upper surface of the atomizing member 1 and the elastic ring 2 that is in contact with the lower surface of the atomizing member 1 are preferably the same in average diameter [(inner diameter+outer diameter)/2], cross-sectional diameter, hardness, and the like, and are particularly preferably the same in average diameter.

Figure 3:
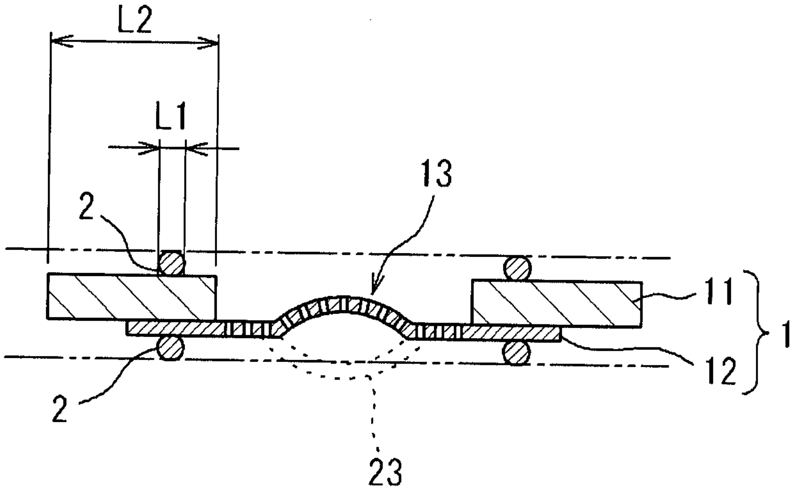
FIG. 3 is a cross-sectional view of a main part of the ultrasonic atomizing unit.

As shown in FIG. 3, on one side in the radial direction from the center of the atomizing member 1, a facing width L1 in the radial direction between each elastic ring 2 and one surface of the atomizing member 1 (hereinafter, referred to as "facing width L1 between the elastic ring 2 and the atomizing member 1") is set so as to be equal to or less than 40% and more preferably 35% of a radial direction width L2 of the piezoelectric vibrator 11 on one side in the radial direction from the center of the piezoelectric vibrator 11 (hereinafter, referred to as "radial direction width L2 of the piezoelectric vibrator 11"). Due to this, suppression of vibrations of the atomizing member 1 can effectively be prevented.

The facing width L1 between the elastic ring 2 and the atomizing member 1 corresponds to the projection width of the elastic ring 2 to the atomizing member 1. When the elastic ring 2 is an O-ring, the facing width L1 is equivalent to the cross-sectional diameter of the O-ring. When the elastic ring 2 is a square ring, the facing width L1 is equivalent to the radial direction width thereof.

The ratio [(L1/L2)·100(%)] of the facing width L1 between the elastic ring 2 and the atomizing member 1 to the radial direction width L2 of the piezoelectric vibrator 11 can easily be set by, for example, decreasing the cross-sectional diameter of the elastic ring 2 or increasing the cross-sectional diameter of the elastic ring 2 in the piezoelectric vibrator 11 having the same size.

The lower limit of the ratio [(L1/L2)·100(%)] of the facing width L1 between the elastic ring 2 and the atomizing member 1 to the radial direction width L2 of the piezoelectric vibrator 11 is selected as appropriate in a range where the atomizing member 1 can stably be supported. The ratio is equal to or higher than 5% and more preferably equal to or higher than 10%. In this case, the atomizing member 1 can stably be supported by the pair of elastic rings 2, and thus a liquid can stably be atomized.

Examples of the material of the elastic rings 2 include nitrile rubber, fluorocarbon rubber, ethylene propylene rubber, silicone rubber, acrylic rubber, and hydrogenated nitrile rubber.

The casing 3 has a hollow annular shape divided into two upper and lower portions that are separable from each other, and is entirely formed from a synthetic resin. The inner diameters of openings 31 in the upper and lower surfaces of the casing 3 are smaller than the inner diameters of the elastic rings 2, in order to allow the elastic rings 2 to be sandwiched and supported between the casing 3 and the atomizing member 1. The elastic rings 2 are also in contact with the inner surface of the casing 3.

The liquid absorbing core 4 is formed from a nonwoven fabric having a diameter of, for example, 3 to 4.5 mm, and a top thereof is adjacent to or in contact with the convex portion 13 of the vibrating plate 12. A lower portion of the liquid absorbing core 4 is immersed in a tank (not shown) that contains a chemical liquid such as a perfuming agent, a germicide, or an insecticide, and the chemical liquid can be supplied to the convex portion 13 due to a capillary phenomenon.

According to the ultrasonic atomizing unit configured as described above, a high-frequency voltage is applied to the piezoelectric vibrator 11 to vibrate the convex portion 13 of the vibrating plate 12, whereby the chemical liquid supplied to the convex portion 13 through the liquid absorbing core 4 is introduced into the micropores 13*a* of the convex portion 13 due to the capillary phenomenon and sprayed upwardly in a state of being atomized.

In this case, since the facing width L1 between the elastic ring 2 and the atomizing member 1 is equal to or less than 40% of the radial direction width L2 of the piezoelectric vibrator 11, suppression of vibrations of the atomizing member 1 by the elastic rings 2 can be prevented. Thus, fine particles of the chemical liquid atomized by the atomizing member 1 can be sprayed farther. For example, when fine particles of a chemical liquid are sprayed upwardly under the same conditions by using the ultrasonic atomizing unit of the present invention and a conventional ultrasonic atomizing unit [(L1/L2)·100=100%] which have convex type vibrating plates, it is confirmed that while the maximum spray height of the conventional ultrasonic atomizing unit is 10 to 15 cm, the maximum spray height of the ultrasonic atomizing unit of the present invention is 2 to 3 times as high as that of the conventional one.

As each annular elastic member 2, instead of the O-ring, a ring whose cross-sectional shape is an ellipse, a rectangle, a triangle, a rhombus, or the like may be used. In addition, a ring whose cross-sectional shape is a D shape, an X shape, a T shape, or the like may be used.

Further, the annular elastic member does not have to be continuous completely in a circumferential direction, may have a cut formed at one location in the circumferential direction, or may have cuts formed intermittently at several locations in the circumferential direction.

The convex portion 13 of the vibrating plate 12 is not limited to a dome-shaped one whose top is formed with a curved surface, and may have a circular cone frustum shape whose top is formed with a planar surface, and the shape of the convex portion 13 is arbitrary.

Further, in the embodiment, as the vibrating plate 12, the convex type vibrating plate in which the convex portion 13 projects in the spray direction is exemplified. However, the vibrating plate 12 may be a concave type vibrating plate having a concave portion 23 projecting in a direction opposite to the spray direction in which the convex portion 13 projects (see a dotted line in FIG. 3). Alternatively, the vibrating plate 12 may be a flat plate type vibrating plate that has no convex portion and no concave portion at a central part thereof.

In the embodiment, the circular thin plate-shaped vibrating plate 12 entirely covers the opening 11*a* of the piezoelectric vibrator 11. However, a rectangular thin plate-shaped vibrating plate may be used, may be arranged so as to extend over the opening 11*a* of the piezoelectric vibrator 11, and may be fixed at both ends thereof to one surface of the piezoelectric vibrator 11.

Figure 4:
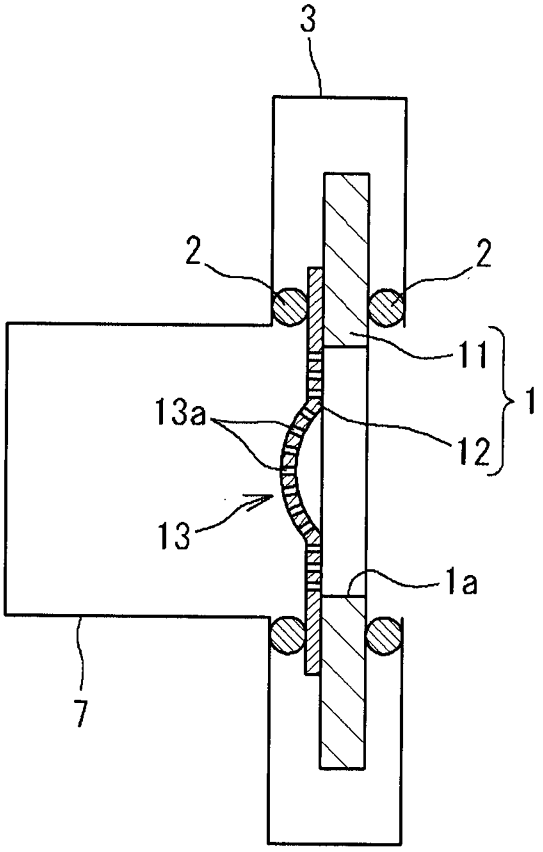
FIG. 4 is a schematic cross-sectional view illustrating another embodiment.
Figure 5:
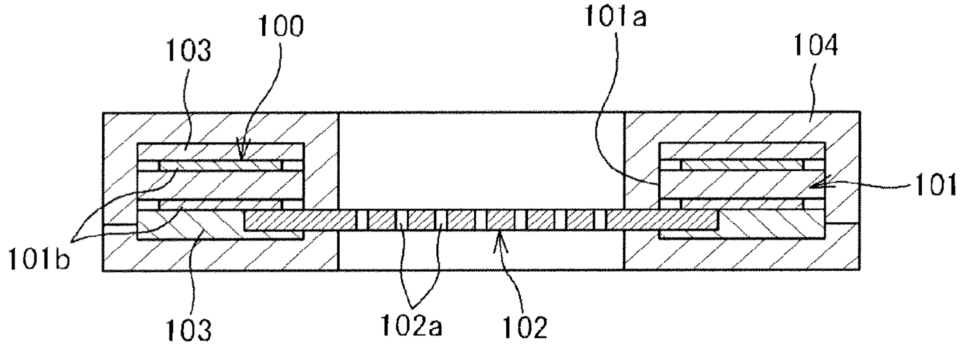
FIG. 5 is a cross-sectional view illustrating a conventional ultrasonic atomizing unit.
Figure 6:
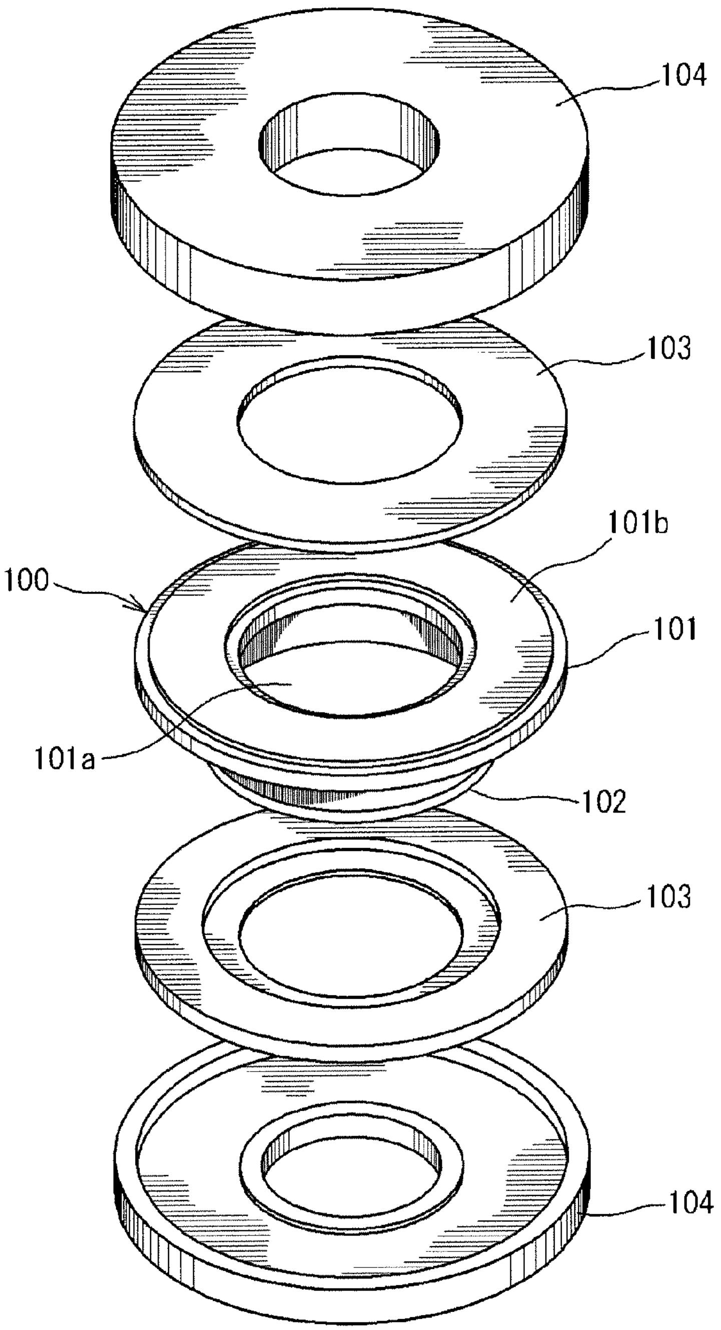
FIG. 6 is an exploded perspective view of the conventional example.
Figure 7:
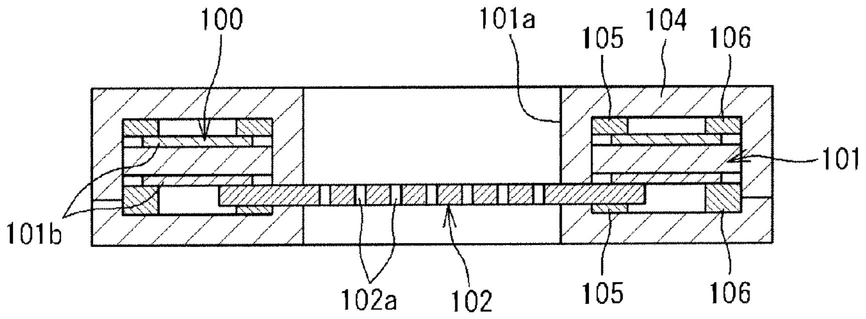
FIG. 7 is a cross-sectional view illustrating another conventional example.

Further, as shown in FIG. 4, the ultrasonic atomizing unit according to the invention can also be applied to a device in which, from a container 7 containing a chemical liquid, the chemical liquid is supplied directly to the vibrating plate 12 without using the liquid absorbing core 4, and be used.

Advantageous Effect Confirmation Test

(1) Advantageous Effect Confirmation Test 1

Examples A1 to A12

As Examples A1 to A12, ultrasonic atomizing units having the following specifications were produced. The ultrasonic atomizing units of these Examples have the same structures as that shown in FIG. 1.

i. Atomizing member

Piezoelectric vibrator:

Piezoelectric ceramic having an outer diameter of 15 mm, an inner diameter of 5 mm, and a thickness of 0.4 mm.

Vibrating plate:

Convex type vibrating plate

The diameter of the base end part of the convex portion is 3 mm.

The pore sizes of micropores are 10 μm.

The thickness is 0.04 mm (made of nickel).

ii. Annular elastic members

O-rings having sizes shown in Table 1 (the hardness is 50 IRHD)

Comparative Examples A1 to A3

As Comparative Examples A1 to A3, ultrasonic atomizing units having the same structures as those in Examples A1 to A12 and having different sizes from those in Examples A1 to A12 were produced. The sizes of the O-rings of these Comparative Examples are shown in Table 1.

The facing ratio (%) shown in Table 1 is a value obtained by dividing the cross-sectional diameter of the O-ring (=the facing width L1 between the O-ring and the atomizing member) by the radial direction width (L2) of the piezoelectric vibrator and multiplying by 100. The same applies to O-rings in other tables.

Test Conditions and Results

The ultrasonic atomizing units of Examples A1 to A12 and Comparative Examples A1 to A3 were used to conduct an advantageous effect confirmation test. In this test, electric power having a voltage of 35 Vp-p and a high frequency of 110 kHz was supplied to the piezoelectric vibrator, and the maximum spray heights of these Examples and these Comparative Examples were measured when a spray liquid was sprayed upwardly.

In addition, as the spray liquid, a petroleum solvent (trade name "EXXSOL D110") was used. The results of the advantageous effect confirmation test are shown in Table 1.

TABLE 1

Convex type vibrating plate, micropore size 10 μm

| Example • Comparative Example | Inner diameter (mm) | Cross-sectional diameter (mm) | Facing ratio (%) | Spray height (cm) |
|---|---|---|---|---|
| Example A1 | 7.0 | 0.5 | 10 | 38 |
| Example A2 | 9.0 | 0.5 | 10 | 38 |
| Example A3 | 10.6 | 0.6 | 12 | 36 |
| Example A4 | 6.5 | 1.0 | 20 | 38 |
| Example A5 | 8.5 | 1.0 | 20 | 37 |
| Example A6 | 10.4 | 1.0 | 20 | 36 |
| Example A7 | 6.0 | 1.5 | 30 | 36 |
| Example A8 | 8.0 | 1.5 | 30 | 36 |
| Example A9 | 10.0 | 1.5 | 30 | 37 |
| Example A10 | 5.5 | 2.0 | 40 | 34 |
| Example A11 | 7.5 | 2.0 | 40 | 34 |
| Example A12 | 9.5 | 2.0 | 40 | 35 |
| Comparative Example A1 | 5.0 | 2.2 | 44 | 27 |
| Comparative Example A2 | 7.0 | 2.2 | 44 | 28 |
| Comparative Example A3 | 9.0 | 2.2 | 44 | 27 |

From Table 1, it is obvious that the spray heights of Examples A1 to A12 are higher than those of Comparative Examples A1 to A3. In other words, it is obvious that when the maximum value of the facing width (L1) between the O-ring and the atomizing member is equal to or less than 40% of the radial direction width (L2) of the piezoelectric vibrator, fine particles of a chemical liquid atomized by the atomizing member can effectively be sprayed far.

(2) Advantageous Effect Confirmation Test 2

Examples B1 to B12

As Examples B1 to B12, ultrasonic atomizing units having the same specifications as those in Examples A1 to A12 except that the pore sizes of the micropores of the vibrating plate are 6 μm, were produced.

Comparative Examples B1 to B3

As Comparative Examples B1 to B3, ultrasonic atomizing units having the same specifications as those in Comparative Examples A1 to A3 except that the pore sizes of the micropores of the vibrating plate are 6 μm, were produced.

Test Conditions and Results

The ultrasonic atomizing units of Examples B1 to B12 and Comparative Examples B1 to B3 were used to conduct an advantageous effect confirmation test under the same conditions as those in the advantageous effect confirmation test 1.

The results of the advantageous effect confirmation test are shown in Table 2.

TABLE 2

Convex type vibrating plate, micropore size 6 μm

| Example • Comparative Example | Inner diameter (mm) | Cross-sectional diameter (mm) | Facing ratio (%) | Spray height (cm) |
|---|---|---|---|---|
| Example B1 | 7.0 | 0.5 | 10 | 38 |
| Example B2 | 9.0 | 0.5 | 10 | 38 |
| Example B3 | 10.6 | 0 6 | 12 | 38 |
| Example B4 | 6.5 | 1.0 | 20 | 39 |
| Example B5 | 8.5 | 1.0 | 20 | 37 |
| Example B6 | 10.4 | 1.0 | 20 | 37 |
| Example B7 | 6.0 | 1.5 | 30 | 37 |
| Example B8 | 8.0 | 1.5 | 30 | 36 |
| Example B9 | 10.0 | 1.5 | 30 | 36 |
| Example B10 | 5.5 | 2.0 | 40 | 33 |
| Example B11 | 7.5 | 2.0 | 40 | 33 |
| Example B12 | 9.5 | 2.0 | 40 | 33 |
| Comparative Example B1 | 5.0 | 2.2 | 44 | 25 |
| Comparative Example B2 | 7.0 | 2.2 | 44 | 26 |
| Comparative Example B3 | 9.0 | 2.2 | 44 | 26 |

From Table 2, it is obvious that the spray heights of Examples B1 to B12, in which the pore sizes of the micropores of the vibrating plate are 6 μm, are also higher than those of Comparative Examples B1 to B3.

(3) Advantageous Effect Confirmation Test 3

Examples C1 to C12

As Examples C1 to C12, ultrasonic atomizing units having the same specifications as those in Examples A1 to A12 except that the pore sizes of the micropores of the vibrating plate are 12 μm, were produced.

Comparative Examples C1 to C3

As Comparative Examples C1 to C3, ultrasonic atomizing units having the same specifications as those in Comparative Examples A1 to A3 except that the pore sizes of the micropores of the vibrating plate are 12 μm, were produced.

Test Conditions and Results

The ultrasonic atomizing units of Examples C1 to C12 and Comparative Examples C1 to C3 were used to conduct an advantageous effect confirmation test under the same conditions as those in the advantageous effect confirmation test 1.

The results of the advantageous effect confirmation test are shown in Table 3.

TABLE 3

Convex type vibrating plate, micropore size 12 μm

| Example • Comparative Example | Inner diameter (mm) | Cross-sectional diameter (mm) | Facing ratio (%) | Spray height (cm) |
|---|---|---|---|---|
| Example C1 | 7.0 | 0.5 | 10 | 38 |
| Example C2 | 9.0 | 0.5 | 10 | 36 |
| Example C3 | 10.6 | 0.6 | 12 | 34 |
| Example C4 | 6.5 | 1.0 | 20 | 37 |
| Example C5 | 8.5 | 1.0 | 20 | 35 |
| Example C6 | 10.4 | 1.0 | 20 | 32 |
| Example C7 | 6.0 | 1.5 | 30 | 34 |
| Example C8 | 8.0 | 1.5 | 30 | 35 |
| Example C9 | 10.0 | 1.5 | 30 | 32 |
| Example C10 | 5.5 | 2.0 | 40 | 31 |
| Example C11 | 7.5 | 2.0 | 40 | 30 |
| Example C12 | 9.5 | 2.0 | 40 | 30 |
| Comparative Example C1 | 5.0 | 2.2 | 44 | 22 |
| Comparative Example C2 | 7.0 | 2.2 | 44 | 23 |
| Comparative Example C3 | 9.0 | 2.2 | 44 | 24 |

From Table 3, it is obvious that the spray heights of Examples C1 to C12, in which the pore sizes of the micropores of the vibrating plate are 12 μm, are also higher than those of Comparative Examples C1 to C3.

(4) Advantageous Effect Confirmation Test 4

Examples D1 to D9

As Examples D1 to D9, ultrasonic atomizing units having the same specifications as those in Examples A1, A5, and A9 except that O-rings having different hardnesses are used, were produced.

Test Conditions and Results

The ultrasonic atomizing units of Examples D1 to D9 were used to conduct an advantageous effect confirmation test under the same conditions as those in the advantageous effect confirmation test 1.

The results of the advantageous effect confirmation test are shown in Table 4. For reference, the test results of Examples A1, A5, and A9 in Table 1 are also shown in Table 4.

TABLE 4

Convex type vibrating plate, micropore size 10 μm

| Example • Comparative Example | Inner diameter (mm) | Cross-sectional diameter (mm) | Facing ratio (%) | Hardness (IRHD) | Spray height (cm) |
|---|---|---|---|---|---|
| Example D1 | 7.0 | 0.5 | 10 | 30 | 39 |
| Example A1 | 7.0 | 0.5 | 10 | 50 | 38 |
| Example D2 | 7.0 | 0.5 | 10 | 80 | 37 |
| Example D3 | 7.0 | 0.5 | 10 | 90 | 37 |
| Example D4 | 8.5 | 1.0 | 20 | 30 | 37 |
| Example A5 | 8.5 | 1.0 | 20 | 50 | 37 |
| Example D5 | 8.5 | 1.0 | 20 | 80 | 36 |
| Example D6 | 8.5 | 1.0 | 20 | 90 | 36 |
| Example D7 | 10.0 | 1.5 | 30 | 30 | 35 |
| Example A9 | 10.0 | 1.5 | 30 | 50 | 37 |
| Example D8 | 10.0 | 1.5 | 30 | 80 | 36 |
| Example D9 | 10.0 | 1.5 | 30 | 90 | 36 |

From Table 4, it is obvious that the spray heights of the ultrasonic atomizing units whose O-rings have the same sizes are substantially the same. Therefore, it is recognized that the hardnesses of the O-rings do not almost influence the spray heights.

(5) Advantageous Effect Confirmation Test 5

Examples E1 to E12

As Examples E1 to E12, ultrasonic atomizing units having the following specifications were produced. The ultrasonic atomizing units of Examples E1 to E12 have the same structures as that shown in FIG. 1, except that a concave type vibrating plate is used.

i. Atomizing member
Piezoelectric vibrator:
Piezoelectric ceramic having an outer diameter of 15 mm, an inner diameter of 5 mm, and a thickness of 0.4 mm.
Vibrating plate:
Concave type vibrating plate
The diameter of the base end part of the concave portion is 3 mm.
The pore sizes of micropores are 10 μm.
The thickness is 0.04 mm (made of nickel).
ii. Annular elastic members
O-rings having sizes shown in Table 5 (the hardness is 50 IRHD)

Comparative Examples E1 to E3

As Comparative Examples E1 to E3, ultrasonic atomizing units having the same structures as those in Examples E1 to E12 and having different sizes from those in Examples E1 to E12 were produced. The sizes of the O-rings of these Comparative Examples are shown in Table 5.

Test Conditions and Results

The ultrasonic atomizing units of Examples E1 to E12 and Comparative Examples E1 to E3 were used to conduct an advantageous effect confirmation test. In this test, electric power having a voltage of 45 Vp-p and a high frequency of 110 kHz was supplied to the piezoelectric vibrator, and the maximum spray heights of these Examples and these Comparative Examples were measured.

In addition, as a spray liquid, a petroleum solvent (trade name "EXXSOL D110") was used. The results of the advantageous effect confirmation test are shown in Table 5.

TABLE 5

Concave type vibrating plate, micropore size 10 μm

| Example • Comparative Example | Inner diameter (mm) | Cross-sectional diameter (mm) | Facing ratio (%) | Spray height (cm) |
|---|---|---|---|---|
| Example E1 | 7.0 | 0.5 | 10 | 28 |
| Example E2 | 9.0 | 0.5 | 10 | 27 |
| Example E3 | 10.6 | 0.6 | 12 | 26 |
| Example E4 | 6.5 | 1.0 | 20 | 28 |
| Example E5 | 8.5 | 1.0 | 20 | 27 |
| Example E6 | 10.4 | 1.0 | 20 | 26 |
| Example E7 | 6.0 | 1.5 | 30 | 27 |
| Example E8 | 8.0 | 1.5 | 30 | 27 |
| Example E9 | 10.0 | 1.5 | 30 | 25 |
| Example E10 | 5.5 | 2.0 | 40 | 24 |
| Example E11 | 7.5 | 2.0 | 40 | 23 |
| Example E12 | 9.5 | 2.0 | 40 | 24 |
| Comparative Example E1 | 5.0 | 2.2 | 44 | 17 |
| Comparative Example E2 | 7.0 | 2.2 | 44 | 17 |
| Comparative Example E3 | 9.0 | 2.2 | 44 | 17 |

From Table 5, it is recognized that when the maximum value of the facing width (L1) between the O-ring and the atomizing member is equal to or less than 40% of the radial direction width (L2) of the piezoelectric vibrator, fine particles of a chemical liquid atomized by the atomizing member can effectively be sprayed far. However, it is recognized that the spray heights of Examples A1 to A12, in which the convex type vibrating plate is used, are higher than those of Examples E1 to E12.

(6) Advantageous Effect Confirmation Test 6

Ultrasonic atomizing units having the same specifications as those in Examples E1 to E12 except that the pore sizes of the micropores of the vibrating plate are 6 μm or 12 μm, were produced, and an advantageous effect confirmation test was conducted under the same conditions as those in the advantageous effect confirmation test 5. As a result, it is confirmed that even when the pore sizes of the micropores of the vibrating plate are 6 μm or 12 μm, the spray heights are substantially equal to those of Examples E1 to E12.

(7) Advantageous Effect Confirmation Test 7

Ultrasonic atomizing units having the same specifications as those in Examples E1 to E12 except that O-rings having IRHD hardnesses of 30, 80, and 90 are used, were produced, and an advantageous effect confirmation test was conducted under the same conditions as those in the advantageous effect confirmation test 1. As a result, the spray heights of the ultrasonic atomizing units whose O-rings have the same sizes were substantially the same. Therefore, it is confirmed that also in the ultrasonic atomizing units in which the concave type vibrating plate is used, the hardnesses of the O-rings do not almost influence the spray heights.

(8) Advantageous Effect Confirmation Test 8

Examples F1 to F12

As Examples F1 to F12, ultrasonic atomizing units having the following specifications were produced. The ultrasonic atomizing units of these Examples have the same structures as that shown in FIG. 1, except that a flat plate type vibrating plate is used.

i. Atomizing member
Piezoelectric vibrator:
Piezoelectric ceramic having an outer diameter of 15 mm, an inner diameter of 5 mm, and a thickness of 0.4 mm.
Vibrating plate:
Flat plate type vibrating plate
The thickness is 0.04 mm (made of nickel).
ii. Annular elastic members
O-rings having sizes shown in Table 6 (the hardness is 50 IRHD)

Comparative Examples F1 to F3

As Comparative Examples F1 to F3, ultrasonic atomizing units having the same structures as those in Examples F1 to F12 and having different sizes from those in Examples F1 to F12 were produced. The sizes of the O-rings of these Comparative Examples are shown in Table 6.

Test Conditions and Results

The ultrasonic atomizing units of Examples F1 to F12 and Comparative Examples F1 to F3 were used to conduct an advantageous effect confirmation test. In this test, electric power having a voltage of 45 Vp-p and a high frequency of 110 kHz was supplied to the piezoelectric vibrator, and the maximum spray heights of these Examples and these Comparative Examples were measured.

In addition, as a spray liquid, a petroleum solvent (trade name "EXXSOL D110") was used. The results of the advantageous effect confirmation test are shown in Table 6.

TABLE 6

Flat plate type vibrating plate, micropore size 10 μm

| Example • Comparative Example | Inner diameter (mm) | Cross-sectional diameter (mm) | Facing ratio (%) | Spray height (cm) |
|---|---|---|---|---|
| Example F1 | 7.0 | 0.5 | 10 | 20 |
| Example F2 | 9.0 | 0.5 | 10 | 20 |
| Example F3 | 10.6 | 0.6 | 12 | 19 |
| Example F4 | 6.5 | 1.0 | 20 | 20 |
| Example F5 | 8.5 | 1.0 | 20 | 20 |
| Example F6 | 10.4 | 1.0 | 20 | 19 |
| Example F7 | 6.0 | 1.5 | 30 | 17 |
| Example F8 | 8.0 | 1.5 | 30 | 19 |
| Example F9 | 10.0 | 1.5 | 30 | 19 |
| Example F10 | 5.5 | 2.0 | 40 | 17 |
| Example F11 | 7.5 | 2.0 | 40 | 16 |
| Example F12 | 9.5 | 2.0 | 40 | 17 |
| Comparative Example F1 | 5.0 | 2.2 | 44 | 12 |
| Comparative Example F2 | 7.0 | 2.2 | 44 | 12 |
| Comparative Example F3 | 9.0 | 2.2 | 44 | 11 |

From Table 6, it is recognized that when the maximum value of the facing width (L1) between the elastic ring and the atomizing member is equal to or less than 40% of the radial direction width (L2) of the piezoelectric vibrator, fine particles of a chemical liquid atomized by the atomizing member can effectively be sprayed far. However, it is recognized that the spray heights of Examples A1 to A12, in which the convex type vibrating plate is used, and of Examples E1 to E12, in which the concave type vibrating plate is used, are higher than those of Examples F1 to F12.

(9) Advantageous Effect Confirmation Test 9

Ultrasonic atomizing units having the same specifications as those in Examples F1 to F12 except that the pore sizes of the micropores of the vibrating plate are 6 μm or 12 μm, were produced, and an advantageous effect confirmation test was conducted under the same conditions as those in the advantageous effect confirmation test 5. As a result, it is confirmed that even when the pore sizes of the micropores of the vibrating plate are 6 μm or 12 μm, the spray heights are substantially equal to those of Examples F1 to F12.

(10) Advantageous Effect Confirmation Test 10

Ultrasonic atomizing units having the same specifications as those in Examples F1 to F12 except that O-rings having IRHD hardnesses of 30, 80, and 90 are used, were produced, and an advantageous effect confirmation test was conducted under the same conditions as those in the advantageous effect confirmation test 1. As a result, the spray heights of the ultrasonic atomizing units whose O-rings have the same sizes were substantially the same. Therefore, it is confirmed that also in the ultrasonic atomizing units in which the flat plate type vibrating plate is used, the hardnesses of the O-rings do not almost influence the spray heights.

(11) Advantageous Effect Confirmation Test 11

As Examples G1 to G6, ultrasonic atomizing units having the following specifications were produced. In the ultrasonic atomizing units of these Examples, a convex type vibrating plate, a concave type vibrating plate, or a flat plate type vibrating plate is used as a vibrating plate, and square rings are used as elastic rings.

i. Atomizing member

Piezoelectric vibrator:

Piezoelectric ceramic having an outer diameter of 15 mm, an inner diameter of 5 mm, and a thickness of 0.4 mm.

Vibrating plate:

a. Convex type vibrating plate

The diameter of the base end part of the convex portion is 3 mm.

b. Concave type vibrating plate

The diameter of the base end part of the concave portion is 3 mm.

c. Flat plate type vibrating plate

The thickness of each of the vibrating plates a to c is 0.04 mm (made of nickel).

The pore sizes of micropores of each of the vibrating plates a to c are 10 μm.

ii. Annular elastic members

Square rings having square cross-sectional shapes and sizes shown in Table 7 (the hardness is 55 IRHD)

Comparative Examples G1 to G3

As Comparative Examples G1 to G3, ultrasonic atomizing units having the same structures as those in Examples G1 to G6 and having different sizes from those in Examples G1 to G6 were produced. The sizes of the square rings of these Comparative Examples are shown in Table 7.

Test Conditions and Results

The ultrasonic atomizing units of Examples G1 to G6 and Comparative Examples G1 to G3 were used to conduct an advantageous effect confirmation test. In this test, electric power having the following voltages and a high frequency of 110 kHz was supplied to the piezoelectric vibrator, and the maximum spray heights of Examples G1 to G6 and Comparative Examples G1 to G3 were measured when a spray liquid was sprayed upwardly.

Convex type vibrating plate: 35 Vp-p

Concave type vibrating plate: 45 Vp-p

Flat plate type vibrating plate: 45 Vp-p

In addition, as the spray liquid, a petroleum solvent (trade name "EXXSOL D110") was used. The results of the advantageous effect confirmation test are shown in Table 7.

The facing ratio (%) shown in Table 7 is a value obtained by dividing the radial direction width of the square ring (=the facing width L1 between the square ring and the atomizing member) by the radial direction width (L2) of the piezoelectric vibrator and multiplying by 100.

TABLE 7

| Square ring, micropore size 10 μm | | | | | |
|---|---|---|---|---|---|
| | Square ring | | | | |
| Example • Comparative Example | Inner diameter (mm) | Radial direction width (mm) | Facing ratio (%) | Type of vibrating plate | Spray height (cm) |
| Example G1 | 8.0 | 1.5 | 30 | Convex type | 36 |
| Example G2 | 7.0 | 2.0 | 40 | Convex type | 34 |
| Comparative Example G1 | 6.6 | 2.2 | 44 | Convex type | 26 |
| Example G3 | 8.0 | 1.5 | 30 | Concave type | 25 |
| Example G4 | 7.0 | 2.0 | 40 | Concave type | 23 |
| Comparative Example G2 | 6.6 | 2.2 | 44 | Concave type | 17 |
| Example G5 | 8.0 | 1.5 | 30 | Flat plate | 19 |
| Example G6 | 7.0 | 2.0 | 40 | Flat plate | 18 |
| Comparative Example G3 | 6.6 | 2.2 | 44 | Flat plate | 12 |

From Table 7, it is obvious that the spray heights of Examples G1 to G6 are higher than those of Comparative Examples G1 to G3. Therefore, it is recognized that even when the square ring whose cross-sectional shape is a rectangle is used as each elastic ring, the same advantageous effects as those when O-rings are used are provided.

REFERENCE SIGNS LIST

1 atomizing member
11 piezoelectric vibrator
11*a* opening
12 vibrating plate
13 convex portion
13*a* micropore
2 elastic ring (elastic member)
3 casing (holding member)
L1 facing width between elastic ring and atomizing member
L2 radial direction width of piezoelectric vibrator

The invention claimed is:

1. An ultrasonic atomizing unit comprising:
an atomizing member comprising:
an annular plate-shaped piezoelectric vibrator having an opening at a central part thereof and having a first annular surface and an opposing second annular surface, and having a radial direction width, and
a vibrating plate comprising a first portion which faces the opening of the piezoelectric vibrator and contains a plurality of micropores extending therethrough in a thickness direction thereof, and a plate-shaped annular portion around the part having the micropores, wherein the annular portion comprises a first surface and an opposing second surface, wherein the first surface is arranged so as to extend along the first annular surface of the piezoelectric vibrator,
the atomizing member being configured to ultrasonically vibrate the vibrating plate with the piezoelectric vibrator to atomize a liquid,
wherein the atomizing member has a first surface containing the second annular surface of the piezoelectric vibrator and a second surface containing the second surface of the annular portion of the vibrating plate;
a first O-ring and a second O-ring, each having a cross-sectional diameter; and
a holding member elastically sandwiching and holding the atomizing member through the first and second O-rings only in a direction perpendicular to the first and second surfaces of the atomizing member,
wherein the first O-ring is arranged so as to extend along the first surface of the atomizing member so as to be concentric with the atomizing member, and the second O-ring is arranged so as to extend along the second surface of the atomizing member so as to be concentric with the atomizing member,
wherein a maximum cross-sectional diameter of each O-ring is 40% of the radial direction width of the piezoelectric vibrator.

2. The ultrasonic atomizing unit according to claim 1, wherein the vibrating plate has, at a central part thereof, a convex portion projecting to a spray side.

3. The ultrasonic atomizing unit according to claim 2, wherein, where a diameter of a base end part of the convex portion is indicated by R1 and a diameter of the opening at the central part of the piezoelectric vibrator is indicated by R2, a relation between R1 and R2 is:

$$R1 \leq (4/5) \cdot R2.$$

4. The ultrasonic atomizing unit according to claim 1, wherein the cross-sectional diameter of each O-ring is 0.5 to 2.0 mm.

5. The ultrasonic atomizing unit according to claim 1, wherein a minimum cross-sectional diameter of each O-ring is 5% of the radial direction width of the piezoelectric vibrator.

6. The ultrasonic atomizing unit according to claim 1, wherein each O-ring has a hardness of 20 to 90 IRHD.

7. The ultrasonic atomizing unit according to claim 1, wherein the holding member includes an upper surface with a central opening and a lower surface with a central opening, and an inner diameter of each of the openings in the upper and lower surfaces of the holding member are smaller than an inner diameter of the first and second O-rings.

8. An ultrasonic atomizing unit comprising:
an atomizing member comprising:
an annular plate-shaped piezoelectric vibrator having an opening at a central part thereof and having a first annular surface and an opposing second annular surface, and having a radial direction width, and
a vibrating plate comprising a first portion which faces the opening of the piezoelectric vibrator and contains a plurality of micropores extending therethrough in a thickness direction thereof, and a plate-shaped annular portion around the part having the micropores, wherein the annular portion comprises a first surface and an opposing second surface, wherein the first surface is arranged so as to extend along the first annular surface of the piezoelectric vibrator,
the atomizing member being configured to ultrasonically vibrate the vibrating plate with the piezoelectric vibrator to atomize a liquid,
wherein the atomizing member has a first surface containing the second annular surface of the piezoelectric vibrator and a second surface containing the second surface of the annular portion of the vibrating plate;
a first O-ring and a second O-ring, each having a cross-sectional diameter; and
a holding member having an upper opening and a lower opening, and elastically sandwiching and holding the atomizing member through the first and second O-rings,
wherein the first O-ring is arranged so as to extend along the first surface of the atomizing member so as to be concentric with the atomizing member, and the second O-ring is arranged so as to extend along the second surface of the atomizing member so as to be concentric with the atomizing member, wherein a maximum cross-sectional diameter of each O-ring is 40% of the radial direction width of the piezoelectric vibrator, and wherein an inner diameter of each of the openings in the upper and lower surfaces of the holding member are smaller than an inner diameter of the first and second O-rings.

9. The ultrasonic atomizing unit according to claim 8, wherein the vibrating plate has, at a central part thereof, a convex portion projecting to a spray side.

10. The ultrasonic atomizing unit according to claim 9, wherein, where a diameter of a base end part of the convex portion is indicated by R1 and a diameter of the opening at the central part of the piezoelectric vibrator is indicated by R2, a relation between R1 and R2 is:

$$R1 \leq (4/5) \cdot R2.$$

11. The ultrasonic atomizing unit according to claim 8, wherein the cross-sectional diameter of each O-ring is 0.5 to 2.0 mm.

12. The ultrasonic atomizing unit according to claim 8, wherein a-minimum cross-sectional diameter of each O-ring is 5% of the radial direction width of the piezoelectric vibrator.

13. The ultrasonic atomizing unit according to claim 8, wherein each O-ring has a hardness of 20 to 90 IRHD.

* * * * *

UNITED STATES PATENT AND TRADEMARK OFFICE

CERTIFICATE OF CORRECTION

PATENT NO. : 9,126,218 B2
APPLICATION NO. : 13/883840
DATED : September 8, 2015
INVENTOR(S) : Takashi Sasaki and Daisuke Takahata It is certified that error appears in the above-identified patent and that said Letters Patent is hereby corrected as shown below:

On the Title page item “[75] Inventors: Takeshi Sasaki; Daisuke Takahata.”

Should read: “[75] Inventors: Takashi Sasaki; Daisuke Takahata.”

Signed and Sealed this
Twenty-sixth Day of January, 2016

Michelle K. Lee

Michelle K. Lee
*Director of the United States Patent and Trademark Office*